United States Patent [19]

Williams

[11] Patent Number: 4,691,701
[45] Date of Patent: Sep. 8, 1987

[54] CARBON DIOXIDE DETECTOR

[76] Inventor: R. Tudor Williams, 3423 Utah Crescent N.W., Calgary, Alberta, Canada, T2N 4A9

[21] Appl. No.: 889,763

[22] Filed: Jul. 28, 1986

[51] Int. Cl.[4] .......................................... A61M 16/00
[52] U.S. Cl. .................................. 128/207.14; 422/85
[58] Field of Search ...................... 128/202.22, 207.14, 128/207.15, 716, 719; 422/85

[56] References Cited

U.S. PATENT DOCUMENTS

| | | | |
|---|---|---|---|
| 2,638,096 | 5/1953 | Waldhaus | 128/202.22 |
| 2,904,033 | 9/1959 | Shane | 128/716 |
| 3,667,475 | 6/1972 | Venturelli et al. | 128/207.14 |
| 4,346,584 | 8/1982 | Boehringer | 128/719 X |
| 4,366,821 | 1/1987 | Wittmaier et al. | 128/719 |
| 4,558,708 | 12/1985 | Labauda et al. | 128/719 |
| 4,558,709 | 12/1985 | Aida et al. | 128/719 |

FOREIGN PATENT DOCUMENTS 345672  6/1930  United Kingdom .......... 128/202.22

Primary Examiner—Lee S. Cohen
Attorney, Agent, or Firm—Nixon & Vanderhye

[57] ABSTRACT

A carbon dioxide detector for determining the correct location of an endotracheal tube following intubation of a patient. The detector includes a housing with a first tubular member for connection to a endotracheal tube or the like, a second tubular member for connection to an anaesthetic circuit and an indicator to indicate the presence of carbon dioxide in the detector. Preferably the indicator is in the form of a transparent disc which sealingly engages an aperture in the housing, the disc having a chemical substance which provides a colour change indication when exposed to carbon dioxide from a patient.

6 Claims, 1 Drawing Figure

U.S. Patent  Sep. 8, 1987  4,691,701
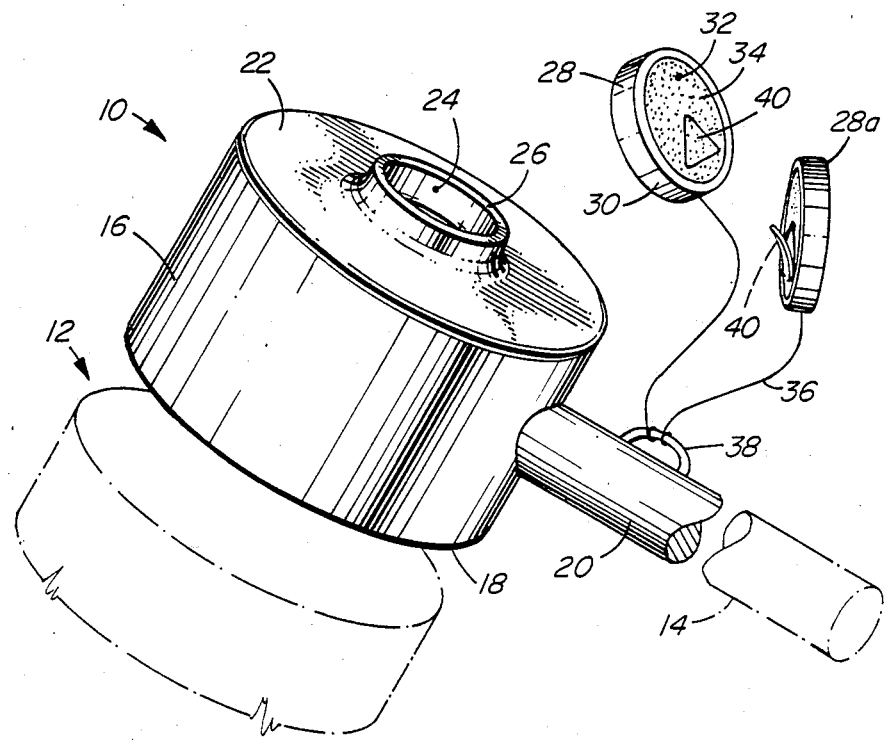

4,691,701

CARBON DIOXIDE DETECTOR

FIELD OF THE INVENTION

This invention relates to $CO_2$ detectors and specifically to a form of a detector which can be used in combination with intubation of a patient by an endotracheal tube to determine whether proper insertion has been made.

BACKGROUND OF THE INVENTION

In surgery, as well as in situations where paramedic personnel are involved, it is commonly necessary to introduce an endotracheal tube into a patient to intubate the trachea and permit the passage of air into and out of the lungs of a patient, thereby aiding in or permitting respiration. During intubation, it is necessary to ascertain that the tube has been properly inserted and has been introduced into the trachea and not into the esophagus.

Paramedics and medical personnel who intubate only occasionally may not be successful in entering the trachea one hundred percent of the time even during visual intubations. Should blind intubation be performed either nasally or orally with the aid of an airway intubator, then the practitioner needs every aid possible to ascertain the correct location of the endotracheal tube. If the tube is in the esophagus there is no return of $CO_2$ and if it is in the trachea, $CO_2$ will be present up to about 5% concentration.

There are several conventional methods of diagnosing the correct placement of an endotracheal tube, such as listening to both sides of the patient's chest with a stethoscope; listening to the abdomen of the patient for air entering the stomach; pressing on the patient's chest and feeling the air coming up the endotracheal tube; seeing condensation on a transparent tube; using quantitive analyzers; and cyanosis during I.P.P.V. with an enlarging distended abdomem (Late sign).

Quantitive analyzers provide accurate readings of the carbon dioxide level but they are expensive and bulky for a practitioner to carry around especially when all that is required is an indication as to whether or not $CO_2$ is present.

SUMMARY OF THE INVENTION

The present invention provides a device to aid practitioners to quickly ascertain the correct location of an endotracheal tube following intubation, a device that will, in one breath of the patient, facilitate the diagnosis of accurate endotracheal tube location.

Essential areas for the use of the present invention are operating rooms, emergency rooms, pediatric intensive care areas and areas involved with infant resuscitation.

According to a broad aspect, the invention relates to a carbon dioxide detector for use with an endotracheal tube or the like or an anaesthetic circuit. The detector comprises a housing having a first tubular member for connection to an endotracheal tube or the like, second tubular member for connection to the anaesthetic circuit, and means for indicating the presence of carbon dioxide in the detector consisting of an aperture in the housing and transparent disc means for sealingly engaging the aperture. The disc means includes a chemical substance which provides a colour change indication when exposed to carbon dioxide in the housing.

Following intubation of a patient, the detector is added to the anaesthetic circuit and one expiration by the patient will instantaneously change the colour of the chemical substance, readily identifying that the trachea has been properly intubated, especially in conjunction with other signs.

Preferably, the connector has a right-angled configuration so that it can fit directly on to the end of an endotracheal tube and the clinician can then look directly down at the indicator disc changing in colour.

One push of the chest of a patient who is not breathing will be sufficient to change the colour of the indicator and if the patient is breathing spontaneously then one expiration is adequate to effect the change.

One form of chemical substance which can be used with this invention is Hydrazine salt, the indicator being a Gentian violet. The discs can contain Litmus paper type material or can be in powder form with a filter on each side thereof. The chemical can also be attached to a transparent disc with a sticky spray or the connector can be a removable disc sealed in an inert atmosphere with the indicator being exposed by removing a sticky metallic flap. The disc is then snapped on to the unit.

BRIEF DESCRIPTION OF THE DRAWING

The invention is illustrated by way of example in the accompanying drawing in which a perspective view of the invention is illustrated.

DESCRIPTION OF THE PREFERRED EMBODIMENT

Referring to the drawing, a carbon dioxide detector indicated generally at 10 is adapted for use with an endotracheal tube 12 or in an anaesthetic circuit encorporating a conduit 14. The detector 10 comprises a housing 16, preferably of cylindrical configuration, and having a tubular opening 18 at one end thereof for a slip-on or snap-on connection to the upper end of the endotracheal tube 12. A second tubular member 20 extends outwardly from the housing 16 and is adapted to connect the housing into an anaesthetic circuit incorporating the conduit 14.

An end wall 22 of the housing 16 is provided with an aperture 24 having a flange or collar 26 which is adapted to receive a disc 28 in a snap-on/snap-off arrangement. The disc 28 is composed of a rim 30 with a transparent surface 32 providing visual indication of a chemical substance 34 within the disc.

The discs may be attached by a thread of plastic or the like 36 to a suitable form of connection such as a ring 38 which is connected to or integral with the tubular member 20.

The discs are sealed in an inert atmosphere and the chemical indicator 34 is exposed by removing a sticky metallic flap 40 (as on disc 28a) and the disc is then snapped on to the collar 26 of the aperture 24.

In operation, the endotracheal tube 12 is connected to the housing 16 via the aperture 18 and the tubular member 20 is connected to the anaesthetic circuit via the conduit 14. The metallic flap 40 is peeled away from one side of the disc and the disc 28 is snapped on to the collar 26 of the housing.

If the endotracheal tube 12 has been inserted into the patient, carbon dioxide which is present in the patient's trachea will be immediately detected and indicated by the colour change in the chemical substance 34. For example, using Hydrazine, the Gentian violet indicator will immediately turn blue thus providing the clinician with a quick indication that the tube 12 has been properly inserted in the trachea.

While the present invention has been described in connection with a specific embodiment thereof and in a specific use, various modifications will occur to those skilled in the art without departing from the spirit and scope of the invention as set forth in the appended claims.

The terms and expressions used in this specification are used as terms of description and not of limitation and there is no intention in the use of such terms and expressions to exclude any equivalents of the features shown and described or portions thereof but it is recognized that various modifications are possible within the scope of the invention claimed.

The embodiments of the invention in which an exclusive property or privilege is claimed are defined as follows:

1. A carbon dioxide detector for use with an endotracheal tube or the like or an anaesthetic circuit comprising:
    a housing having a first tubular member for connection to a endotracheal tube or the like;
    a second tubular member for connection to said anaesthetic circuit, said first and second tubular members being in communication with the interior of said housing; and
    means for indicating the presence of carbon dioxide in said detector comprising an aperture in said housing and in communication with said interior thereof and transparent disc means for sealingly engaging said aperture and thereby being in communication with said housing interior;
    said disc means including a chemical substance which provides a colour change indication when exposed to carbon dioxide in said housing.

2. A detector according to claim 1 wherein said housing aperture has a circular collar and said disc means has an on/off snap fit on said collar.

3. A detector according to claim 1 wherein said disc means including surfaces sealing said chemical substance and a removable flap on at least one of said sealing surfaces to expose said substance to said housing aperture.

4. A detector according to claim 1 wherein said chemical substance is Hydrazine salt.

5. A detector according to claim 1 wherein said disc means is formed of litmus paper type material.

6. A detector according to claim 1 wherein said disc means is formed of a powder with a filter means on either side thereof for retaining said powder therebetween.

* * * * *